(12) United States Patent
Song (10) Patent No.: US 10,525,135 B2
(45) Date of Patent: Jan. 7, 2020

(54) LIPOSOME COMPOSITION USING SUGAR ALCOHOL WITH MODIFIED SURFACE AREA AND/OR POROSITY AS CARRIER AND METHOD FOR PREPARING SAME

(71) Applicant: SOONCHUNHYANG UNIVERSITY INDUSTRY ACADEMY COOPERATION FOUNDATION, Chungcheongnam-do (KR)

(72) Inventor: Keon-Hyoung Song, Chungcheongnam-do (KR)

(73) Assignee: SOONCHUNHYANG UNIVERSITY INDUSTRY ACADEMY COOPERATION FOUNDATION, Chungcheongnam-Do (KR)

( * ) Notice: Subject to any disclaimer, the term of this patent is extended or adjusted under 35 U.S.C. 154(b) by 0 days.

(21) Appl. No.: 15/546,416

(22) PCT Filed: Jul. 1, 2015

(86) PCT No.: PCT/KR2015/006774
§ 371 (c)(1),
(2) Date: Nov. 7, 2017

(87) PCT Pub. No.: WO2016/122057
PCT Pub. Date: Aug. 4, 2016

(65) Prior Publication Data
US 2018/0071392 A1 Mar. 15, 2018

(30) Foreign Application Priority Data

Jan. 28, 2015 (KR) .................... 10-2015-0013399

(51) Int. Cl.
| A61K 47/26 | (2006.01) |
| A61K 8/34 | (2006.01) |
| A61K 8/60 | (2006.01) |
| A61K 9/127 | (2006.01) |
| G01N 25/48 | (2006.01) |

(52) U.S. Cl.
CPC .............. *A61K 47/26* (2013.01); *A61K 8/345* (2013.01); *A61K 8/60* (2013.01); *A61K 9/1271* (2013.01); *G01N 25/4866* (2013.01)

(58) Field of Classification Search
None
See application file for complete search history.

(56) References Cited

U.S. PATENT DOCUMENTS

| 2,315,699 A * | 4/1943 | Goepp, Jr. ........... B01D 9/0036 568/868 |
| 2005/0118217 A1* | 6/2005 | Barnhart ................ A61K 9/006 424/401 |

FOREIGN PATENT DOCUMENTS

| EP | 0119020 A2 | 9/1984 |
| KR | 20040074052 A | 8/2004 |
| KR | 20110072996 A | 6/2011 |
| KR | 20140110329 A | 9/2014 |

OTHER PUBLICATIONS

Keon-Hyoung Song, Preparation and evaluation of proliposomes containing salmon calcitonin, Journal of Controlled Release, vol. 84, Issues 1-2, pp. 27-37 (Year: 2002).*
Gupta, Vandana et al., "Formulation Development and in vitro Characterization of Proliposomes for Topical Delivery of Aceclofenac", Indian J. Pharm. Sci., Nov. 2008, pp. 768-775, vol. 70, Issue 6, Copyright Indian Journal of Pharmaceutical Sciences (2008); http://www.ncbi.nlm.nih.gov/pmc/articles/PMC3040871/.
Song, Keon-Hyoung, "Pore-Enhanced Sorbitol Particles as a Drug Carrier of Proliposomal Formulations", International Conference of the Korean Society of Pharmaceutical Sciences and Technology, Nov. 28, 2014, pp. 160-162, sPFD-005.
Supplementary European Search Report dated Aug. 7, 2018 for European Application No. 15880237 filed Jul. 1, 2015.

* cited by examiner

*Primary Examiner* — Celeste A Roney
(74) *Attorney, Agent, or Firm* — Blue Filament Law PLLC

(57) ABSTRACT

The present disclosure relates to a method for preparing a novel sugar alcohol with a modified, that is, increased or decreased surface area and/or porosity while having flowability as a solid phase, and also to a sugar alcohol prepared by the preparing method or a pharmaceutical composition, a cosmetic composition, a food composition and a feed composition, comprising the sugar alcohol as a carrier. According to the present disclosure, the method for preparing a sugar alcohol comprises: (A) reacting the sugar alcohol in a solid state with a solvent (S), wherein the solid state sugar alcohol is not dissolved by the solvent (S) and is reacted with the solvent (S) as a solid dispersion; and (B) removing the solvent (S) therefrom. The sugar alcohol prepared by the preparing method of the present disclosure has a modified, that is, increased or decreased surface area and/or porosity in comparison with a conventional sugar alcohol. When the sugar alcohol prepared by the preparing method of the present disclosure is used as a carrier, a coating object, etc., or as a component of compositions for drugs, food, cosmetics, feed, etc., a ratio of an active ingredient to the carrier can be modified, so that the sugar alcohol can be used in preparing of formulations or compositions.

13 Claims, 7 Drawing Sheets

FIG. 1-A Sorbitol

FIG. 1-B Sorbitol after reacting with methanol

FIG. 1-C Sorbitol after reacting with ethanol

FIG. 1-D Sorbitol after reacting with propanol

FIG. 1-E Sorbitol after reacting with butanol

FIG. 1-F Sorbitol after reacting with acetic acid

FIG. 2-A Mannitol

FIG. 2-B Mannitol after reacting with acetic acid

FIG. 3-A Xylitol

FIG. 3-B Xylitol after reacting with methanol

FIG. 3-C Xylitol after reacting with phenol

FIG. 4-A Sorbitol after reacting with methanol and water (at a ratio of 9:1)

FIG. 4-B Sorbitol after reacting with methanol and water (at a ratio of 99:1)

FIG. 5-A Sorbitol after reacting with chloroform

FIG. 5-B Sorbitol after reacting
with chloroform and methanol (at a ratio of 3:1)

FIG. 5-C Sorbitol after reacting
with chloroform and water (at a ratio of 99:1)

FIG. 6-A Sorbitol manufactured according to Example 11

FIG. 6-B Sorbitol manufactured according to Comparative Example 5

LIPOSOME COMPOSITION USING SUGAR ALCOHOL WITH MODIFIED SURFACE AREA AND/OR POROSITY AS CARRIER AND METHOD FOR PREPARING SAME

TECHNICAL FIELD

The present disclosure relates to a proliposomee composition using a sugar alcohol with a modified surface area and/or porosity as a carrier and a method for preparing the same. Also, the present disclosure relates to a preparing method for adjusting, that is, increasing or decreasing a surface area and porosity of a sugar alcohol, used as a carrier, and relates to the sugar alcohol with the increased or decreased surface area and porosity. The sugar alcohol according to the invention, which can be used as a carrier or coating object, etc., shows transport capabilities modified as a carrier for drugs, cosmetics, food, feed or the like.

BACKGROUND

A proliposomee is a solid preparation with a high flowability, which is prepared by penetrating a volatile solvent dissolved with a drug and a lipid into a porous area inside a water-soluble solid carrier particle, and the proliposomee preparation forms a liposome preparation encapsulating the drug immediately upon coming into contact with water. The proliposomee preparation takes on a solid powder state with a high flowability, thus having an advantage in solving a stability issue raised from a liquid-type liposome preparation. A carrier used in the proliposomee preparation needs to be water-soluble and highly porous, so sugar alcohols are typically often used.

A sugar alcohol, which is a sugar derivative prepared by reducing a carbonyl group of monosaccharides or starches, is mannitol, sorbitol, xylitol, erythritol, arabitol, maltitol, inositol, lactitol, isomalt, fucitol, etc. The sugar alcohol has been widely used in medicines, cosmetics, food, feed, etc. as an additive, an excipient, a sweetener, a wetting agent, a stabilizer, a thickener, etc. Furthermore, the sugar alcohol has been used as a dietary limit or a caries preventative agent or has also been used more and more as a carrier or a coating object for developing a preparation or a formulation by using a high water solubility thereof.

The reason for which the sugar alcohol is used as the carrier or the coating object is associated with the porosity of a sugar alcohol powder particle. In other words, as the surface area and pore of the sugar alcohol powder particle increases, a content of a component to be transported, including an active ingredient or a coating component will increase, too.

Thus, in the researches on improving a surface area and porosity of the sugar alcohol powder particle, this particle is very highly used as a novel carrier or coating object in various fields like medicines, cosmetics, food, feed, etc.

Also, according to the present disclosure, a content of the component to be transported, such as an active ingredient a coating component, etc., can be modified by reducing the surface area and porosity of the sugar alcohol.

DETAILED DESCRIPTION OF THE INVENTION

Technical Problem

The present disclosure provides a novel sugar alcohol with enhanced or decreased transport capabilities as a carrier or a coating object by modifying physical properties such as porosity and surface area of the sugar alcohol while maintaining chemical properties such as water solubility of the sugar alcohol not only as a carrier for a proliposomee preparation but also as other carrier or coating object requiring a soluble solid particle with a porous property, as well as a method for preparing the same. Also, the present disclosure provides a pharmaceutical composition, a food composition, a cosmetic composition or a feed composition, which use the sugar alcohol prepared from the preparing method of the present disclosure as a carrier.

Technical Solvent

The present disclosure provides a proliposomee composition comprising a novel sugar alcohol, as a carrier, with a modified, that is, increased or decreased surface area and/or porosity while having flowability as a solid phase. Also, the present disclosure provides a carrier, which is a novel sugar alcohol with a modified, that is, increased or decreased surface area and/or porosity while having flowability as a solid phase. A method for preparing the proliposomee composition or the sugar alcohol used as a carrier thereof is as described below.

The present disclosure provides a method for preparing a novel sugar alcohol with a modified surface area and/or porosity while having flowability as a solid phase. According to the preparing method of the present disclosure, provided is a sugar alcohol with an increased surface and/or porosity while having flowability as a solid phase depending on a type of sugar alcohol and solvent, a reaction condition, etc., and also provided is a sugar alcohol with a decreased surface area and/or porosity while having flowability as a solid phase.

According to the present disclosure, the method for preparing a novel sugar alcohol with a modified surface area and/or porosity comprises the following steps: (A) reacting the sugar alcohol in a solid state with a solvent (S), in which the sugar alcohol is not completely dissolved by the solvent and is reacted with the solvent (S) as a solid dispersion form; and (B) removing the solvent (S) therefrom.

In the step (A) of the present disclosure, a mass/volume ratio of the sugar alcohol and the solvent (S) can be modified so that the sugar alcohol can sufficiently react to the solvent.

In the step (A) of the present disclosure, a type of the solvent (S) and the sugar alcohol can be modified to react as a solid dispersion state, in which the sugar alcohol is not completely dissolved in the solvent.

Also, in the step (A) of the present disclosure, it is possible to use all the methods for having the sugar alcohol come into contact with the solvent, for example, stirring and mixing the sugar alcohol in the solvent (S).

According to an embodiment of the present disclosure, in the step (A), a reaction between the sugar alcohol and the solvent (S) can be promoted by means of stirring, wherein the stirring can be a conventional stirring process or the stirring process can be also omitted.

Also, in the step (A), a reaction time can be modified so that the sugar alcohol can maintain a solid dispersion state. The reaction time can be preferably one or more minutes, more preferably one minute to ten hours, and even more preferably one or more minutes and one hour or less, but is not limited thereto.

Moreover, the step (A) can be performed at a temperature, at which the sugar alcohol can maintain a solid state. The temperature can be preferably at a room temperature (10-30°

C.) and more particularly at an ambient temperature (15-25° C.), but is not limited thereto.

According to the present disclosure, the step (B) can be performed in such a way that the solvent is left alone at room temperature (10-30° C.) or at ambient temperature (15-25° C.) so as to evaporate the organic solvent. Conventionally applicable drying methods such as hot air drying, freeze-drying and drying under the reduced pressure can be used alone or in a combination thereof, and can be also performed together with stirring.

According to an embodiment of the present disclosure, it is possible to prepare the sugar alcohol with the modified, that is, increased or decreased surface area and/or porosity by reacting the sugar alcohol with the solvent (S), in which the sugar alcohol is not completely dissolved in the solvent and is reacted and stirred with the solvent (S) as a solid dispersion form, and then removing the solvent (S) therefrom. The reaction process, the stirring process and the solvent-removing process can be performed sequentially or simultaneously.

The sugar alcohol used in the present disclosure can be a sugar alcohol, which is a solid state at room temperature (10-30° C.), and preferably a sugar alcohol, which is a water-soluble and solid state at ambient temperature (15-25° C.).

As a detailed example, the sugar alcohol can be mannitol, sorbitol, xylitol, erythritol, arabitol, maltitol, inositol, lactitol, isomalt, fucitol, or a mixture thereof, and preferably can be mannitol, sorbitol, xylitol or a mixture thereof, but is not limited thereto.

Meanwhile, the solvent (S) used in the present disclosure can be an organic solvent (S-1) or a water-mixed organic solvent (S-2).

According to an embodiment of the present disclosure, the solvent (S) can be an organic solvent (S-1).

The organic solvent (S-1), which has to be used by 30 mL or more to dissolve 1 g of the sugar alcohol at 20±5° C., can be a single or mixed solvent. In other words, the organic solvent (S-1) is preferably one of the organic solvents, belonging to "sparingly soluble (30 mL or more and less than 100 mL)," "slightly soluble (100 mL or more and less than 1000 mL)," "very slightly soluble (1000 mL or more and less than 10 L)" or "practically insoluble (10 L or more) according to the labeling terms of solubility as shown in the $10^{th}$ Revision of Korean Pharmacopeia, or a mixture thereof.

In case of using the organic solvent (S-1) in the present disclosure, in the step (A), a reaction time of the sugar alcohol and the organic solvent (S-1) can be modified depending on a reaction temperature, but can be preferably one or more minutes and more preferably 30 minutes or more so that the sugar alcohol and the organic solvent (S-1) can react to each other sufficiently.

In order to prepare the sugar alcohol with the increased surface area and/or porosity while having flowability as a solid phase, the organic solvent (S-1) is preferably a polar organic solvent, wherein the polar organic solvent can be a single solvent or a mixture including the same, and a polarity thereof is preferably 30 to 90% (v/v) of water, but is not limited thereto. As a detailed example, the organic solvent (S-1) can be C1-C5 alcohols, C6-C10 aromatic alcohols, C1-C5 amino alcohols, C1-C4 carboxylic acids, C1-C4 amides or a mixture thereof, preferably C1-C4 alcohols, acetic acid, acetamide, phenol or a mixture thereof, and more preferably C1-C4 alcohols, but is not limited thereto. Furthermore, according to another embodiment of the present disclosure, the solvent (S) can be a water-mixed organic solvent (S-2). The water-mixed organic solvent (S-2) can be a mixture of water and the organic solvent (S-1), and preferably a mixture of water and C1-C4 alcohols.

In order to prepare the sugar alcohol with the decreased surface area and/or porosity while having flowability as a solid phase, the organic solvent (S-1) is preferably a non-polar organic solvent or a mixed solvent including the same, more preferably chloroform or a mixed solvent including the same, and most preferably chloroform or a mixed solvent of chloroform and C1-C4 alcohols, but is not limited thereto. Furthermore, according to another embodiment of the present disclosure, the solvent (S) can be a water-mixed organic solvent (S-2). The water-mixed organic solvent (S-2) can be a mixture of water and the non-polar organic solvent, and preferably a mixture of water and chloroform.

In order to prepare the sugar alcohol with the modified surface area and/or porosity while having flowability as a solid phase, in the water-mixed organic solvent (S-2) of the present disclosure, a volume ratio of water and the organic solvent (S-1) is so selected that a ratio of water amounts to preferably less than 50% (v/v) of the total solvent, more preferably 10% (v/v) or less and even more preferably 1% (v/v) or less. In case of using the water-mixed organic solvent (S-2), a reaction time with the sugar alcohol can vary depending on a content of water and a reaction temperature. However, the reaction time can be preferably one hour or less, more preferably 30 minutes or less, and even more preferably one minute or less. In other words, in case of using the water-mixed organic solvent (S-2), if a ratio of water is high or a reaction time is long, the sugar alcohol can be dissolved, thus not maintaining a solid dispersion thereof. Therefore, in the water-mixed organic solvent, the ratio of water, the reaction time and the like need to be modified according to an amount of the sugar alcohol so that the sugar alcohol cannot be completely dissolved in the solvent and maintain the solid dispersion. According to an embodiment of the present disclosure, if at least 50% (v/v) of water is included in the mixed solvent, the sugar alcohol is conventionally dissolved, thus not obtaining the sugar alcohol with the modified surface area and/or porosity, but is not limited thereto. Also, if the sugar alcohol is reacted as the solid dispersion when at least 50% (v/v) of water is included in the mixed solvent, the surface area and/or porosity thereof can be modified.

The sugar alcohol prepared according to the preparing method of the present disclosure has the significantly increased or decreased surface area and/or porosity in comparison with a conventional sugar alcohol, while maintaining flowability and water solubility as a solid phase.

Therefore, the sugar alcohol prepared according to the preparing method of the present disclosure can be used as a single composition or a component of a pharmaceutical composition, a food composition, a cosmetic composition, a feed composition, etc. in a field that needs or adjusts a porosity property as a carrier or coating object. Furthermore, according to the present disclosure, an example of the pharmaceutical composition can be a proliposomee formulation.

Advantageous Effects

A sugar alcohol prepared according to a preparing method of the present disclosure can have a modified surface area and/or porosity in comparison with a conventional sugar alcohol. In other words, by increasing a surface area and/or pore of a particle, the sugar alcohol as a carrier can encapsulate or deliver an active ingredient, indicate a higher content of a coating component when the coating component is coated. Also, a content of the active ingredient or the coating component can be modified by reducing the surface area and/or pore of the particle. Therefore, the sugar alcohol containing each of the components can be used as a carrier or coating object. Also, when the sugar alcohol is used as a component of compositions such as drugs, cosmetics, food and feed, a ratio of the active ingredient to the carrier can be modified so that the sugar alcohol can be used in preparing a formulation/preparation or a composition.

BEST MODE FOR CARRYING OUT THE PRESENT DISCLOSURE

Hereinafter, in order to help understanding the present disclosure, the embodiments of the present disclosure will be described in greater detail with reference to the following examples. However, the following Examples are provided only for the purpose of illustrating the present disclosure, and thus the scope of the present disclosure is not limited thereto. The examples of the present disclosure are provided for better understanding of the invention to those skilled in the art.

<Example 1> Preparing of a Sorbitol Particle with an Increased Surface Area and/or Porosity by Reacting with Methanol A sorbitol with 212-300 μm size (Sigma-Aldrich, St. Louis, Mo.) was obtained by using a sieve (sieve no. 50 and 70) as provided in the 10$^{th}$ Revision of Korean Pharmacopeia. The sorbitol of 10 g was put into a rotary evaporator (Eyela, Japan) connected with a pressure reducing device along with 30 ml of methanol, and the resulting mixture was stirred at 40 rpm without reducing pressure for 30 minutes, so that the sorbitol and the methanol can react with each other sufficiently. During the reaction, the sorbitol maintained a solid dispersion form. In 30 minutes later, the solvent was completely removed therefrom through reducing pressure and freeze drying, so the sorbitol with the increased surface area and/or porosity while having flowability as a solid phase was obtained.

<Example 2> Preparing of a Sorbitol Particle with an Increased Surface Area and/or Porosity by Reacting with Methanol A reaction time was set to 60 minutes differently from the reaction time of Example 1 and the remaining conditions were the same as Example 1 so that a sorbitol can maintain a solid dispersion form during the reaction time. Accordingly, the sorbitol with the increased surface and/or porosity while having flowability as a solid phase was obtained.

<Examples 3 to 6> Preparing of a Sorbitol Particle with an Increased Surface Area and/or Porosity by Reacting with C2-C4 Alcohol or Acetic Acid Instead of the methanol of Example 1 or 2, C2-C4 alcohols or acetic acid (Sigma-Aldrich, St. Louis, Mo.) was used respectively. As for the remaining conditions, the conditions for ethanol, propanol and acetic acid were the same as Example 1 and the conditions for butanol were the same as Example 2 so that the sorbitol can maintain a solid dispersion form during a reaction time. Therefore, the sorbitol with the increased surface and/or porosity while having flowability as a solid phase was obtained [ethanol (Example 3), propanol (Example 4), butanol (Example 5), and acetic acid (Example 6)].

<Example 7> Preparing of a Mannitol Particle with an Increased Surface Area and/or Porosity by Reacting with Acetic Acid Instead of the sorbitol of Example 6, a mannitol (Sigma-Aldrich, St. Louis, Mo.) was used and the remaining conditions were the same as Example 6 so that the mannitol can maintain a solid dispersion form during a reaction time. Accordingly, the mannitol with the increased surface and/or porosity while having flowability as a solid phase was obtained.

<Example 8> Preparing of a Xylitol Particle with an Increased Surface Area and/or Porosity by Reacting with Methanol Instead of the sorbitol of Example 1, a xylitol (Sigma-Aldrich, St. Louis, Mo.) was used and the remaining conditions were the same as Example 1 so that the xylitol can maintain a solid dispersion form during a reaction time.

Accordingly, the xylitol with the increased surface and/or porosity while having flowability as a solid phase was obtained.

<Example 9> Preparing of a Xylitol Particle with an Increased Surface Area and/or Porosity by Reacting with Phenol Instead of the methanol and the sorbitol of Example 1, a phenol (Sigma-Aldrich, St. Louis, Mo.) and a xylitol were used respectively and the remaining conditions were the same as Example 1 so that the xylitol can maintain a solid dispersion form during a reaction time. Accordingly, the xylitol with the increased surface and/or porosity while having flowability as a solid phase was obtained.

<Example 10> Preparing of a Sorbitol Particle with an Increased Surface Area and/or Porosity by Reacting with a Mixed Solvent of Methanol and Water (at a Ratio of 9:1)

A water-mixed organic solvent was prepared by mixing methanol and water at a ratio of 9:1 (v/v). A sorbitol of 10 g with 212-300 µm size was put into a rotary evaporator by using a sieve (sieve no. 50 and 70), 30 ml of the prepared water-mixed organic solvent was put thereinto, and the resulting mixture was stirred at 50 rpm so that the sorbitol and the water-mixed organic solvent can react with each other sufficiently. During the reaction, the sorbitol maintained a solid dispersion form. In one minute later, the solvent was completely removed therefrom through a freeze drying, so the sorbitol with the increased surface area and/or porosity while having flowability as a solid phase was obtained.

<Example 11> Preparing of a Sorbitol Particle with an Increased Surface Area and/or Porosity by Reacting with a Mixed Solvent of Methanol and Water (at a Ratio of 99:1)

A water-mixed organic solvent was prepared by mixing methanol and water at a ratio of 99:1 (v/v). A sorbitol of 10 g with 212-300 µm size was put into a rotary evaporator by using a sieve (sieve no. 50 and 70), 30 ml of the prepared water-mixed organic solvent was put thereinto, and the resulting mixture was stirred at 50 rpm so that the sorbitol and the water-mixed organic solvent can react with each other sufficiently. During the reaction, the sorbitol maintained a solid dispersion form. In 30 minutes later, the solvent was completely removed therefrom through a freeze drying, so the sorbitol with the increased surface area and/or porosity while having flowability as a solid phase was obtained.

<Example 12> Preparing of a Sorbitol Particle with a Decreased Surface Area and/or Porosity by Reacting with Chloroform A sorbitol with 212-300 µm size was obtained (Sigma-Aldrich, St. Louis, Mo.) by using a sieve (sieve no. 50 and 70) as provided in the 10$^{th}$ Revision of Korean Pharmacopeia. The sorbitol of 10 g was put into a rotary evaporator (Eyela, Japan) connected with a reducing pressure device along with 30 ml of chloroform (Sigma-Aldrich, St. Louis, Mo.), and the resulting mixture was stirred at 50 rpm without reducing pressure so that the sorbitol and the chloroform can react with each other sufficiently. During the reaction, the sorbitol maintained a solid dispersion form. In one minute later, the chloroform was completely removed therefrom through a drying under the reduced pressure, so the sorbitol obtained showed a decreased pore on a surface thereof. Accordingly, the sorbitol with the decreased surface area and/or porosity while having flowability as a solid phase was obtained.

<Example 13> Preparing of a Sorbitol Particle with a Decreased Surface Area and/or Porosity by Reacting with a Mixed Solvent of Chloroform and Methanol (at a Ratio of 3:1)

A sorbitol with 212-300 µm size was obtained (Sigma-Aldrich, St. Louis, Mo.) by using a sieve (sieve no. 50 and 70) as provided in the 10$^{th}$ Revision of Korean Pharmacopeia. The sorbitol of 10 g was put into a rotary evaporator (Eyela, Japan) connected with a reducing pressure device along with 30 ml of a mixed organic solvent of chloroform and methanol (at a ratio of 3:1, v/v) (Sigma-Aldrich, St. Louis, Mo.), and the resulting mixture was stirred at 50 rpm without reducing pressure so that the sorbitol and the mixed organic solvent can react with each other sufficiently. During the reaction, the sorbitol maintained a solid dispersion form. In 60 minutes later, the chloroform was completely removed therefrom through a drying under the reduced pressure. Accordingly, the sorbitol with the decreased surface area and/or porosity while having flowability as a solid phase was obtained.

<Example 14> Preparing of a Sorbitol Particle with a Decreased Surface Area and/or Porosity by Reacting with a Mixed Solvent of Chloroform and Water (at a Ratio of 99:1)

A sorbitol was reacted for 30 minutes by using a solvent of mixing chloroform and water at a ratio of 99:1 (v/v) instead of the chloroform and methanol of Example 13. The remaining conditions were the same as Example 13 so that the sorbitol can maintain a solid dispersion form during a reaction time. Accordingly, the sorbitol with the decreased surface and/or porosity while having flowability as a solid phase was obtained.

Figure 1:
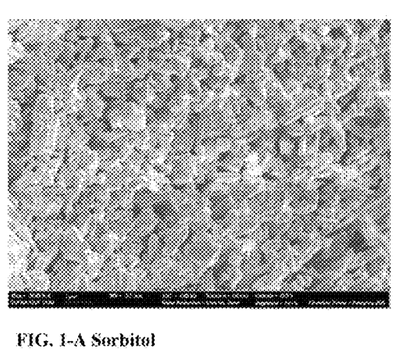
FIG. 1 shows a scanning electron microscope (SEM) image of a conventional sorbitol (FIG. 1-A) and an SEM image of a sorbital prepared after reacting with each organic solvent (FIGS. 1-B, C, D, E and F) according to a preparing method of the present disclosure.
Figure 2:
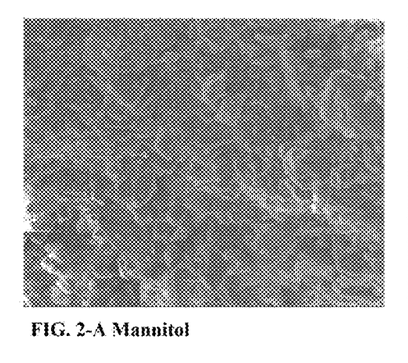
FIG. 2 shows an SEM image of a conventional mannitol (FIG. 2-A) and an SEM image of a mannitol prepared after reacting with acetic acid (FIG. 2-B) according to a preparing method of the present disclosure.
Figure 3:
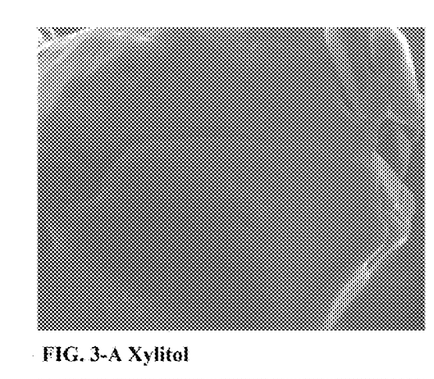
FIG. 3 shows an SEM image of a conventional xylitol (FIG. 3-A) and an SEM image of a xylitol prepared after reacting with each organic solvent (FIGS. 3-B and C) according to a preparing method of the present disclosure.
Figure 4:
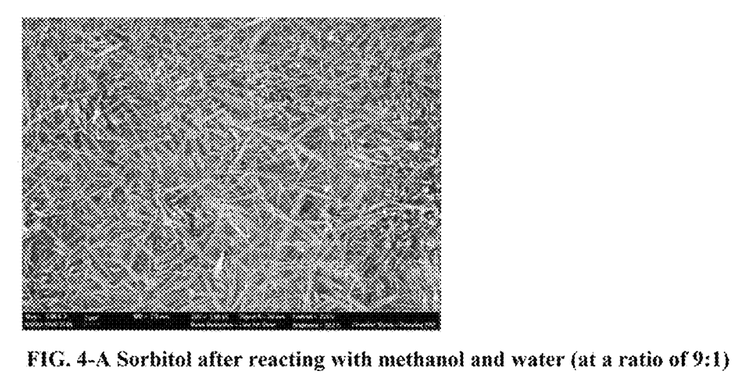
FIG. 4 shows an SEM image of a sorbitol prepared after reacting with a water-mixed solvent of water and methanol (FIGS. 4-A and B) according to a preparing method of the present disclosure.
Figure 5:
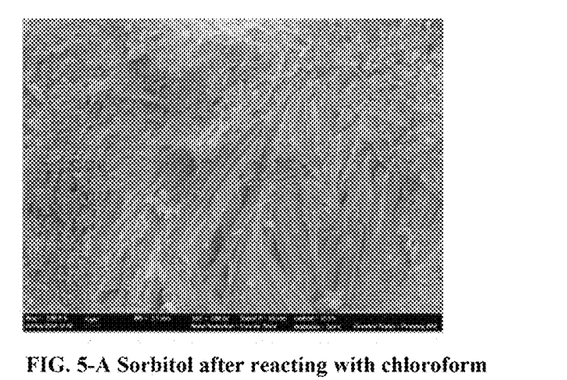
FIG. 5 shows an SEM image of a sorbitol prepared after reacting with chloroform or a mixed solvent including the same according to a preparing method of the present disclosure.
Figure 6:
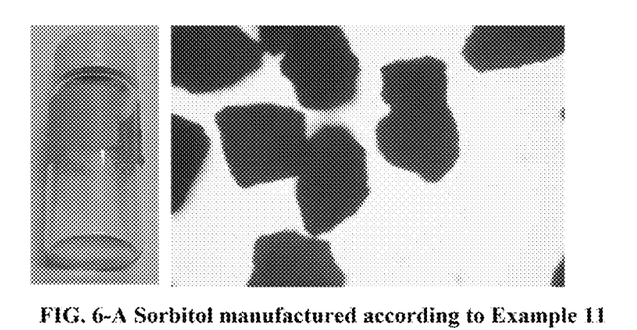
FIG. 6 is an image of a sorbitol prepared according to Example 11 and an image of a sorbitol prepared according to Comparative Example 5, obtained by observing a property thereof with visual inspection and an optical microscope.

<Example 15> Preparing of a Pharmaceutical Composition to Contain a Drug by Using the Sorbitol with the Increased Surface Area and/or Porosity Prepared in Example 1 as a Carrier By using a sieve (sieve no. 50 and 70), the sorbitol with the increased porosity prepared in Example 1 was obtained, thus having a 212-300 µm size. Out of the sorbitol with the increased surface area and/or porosity prepared in Example 1, 3 g of the sorbitol having a 212-300 µm size was put into a rotary evaporator, and the resulting mixture was stirred at 60 rpm with reducing pressure. 4 mg of Sudan IV (Sigma-Aldrich, St. Louis, Mo.) as a drug and 400 mg of phosphatidyl choline (Sigma-Aldrich, St. Louis, Mo.) as a phospholipid were dissolved in an organic solvent, and the resulting mixture was sprayed to the sorbitol in small portions. The Sudan IV and the phospholipid were introduced into a porous structure of the sorbitol without a reaction having an effect on the surface and the porosity of the sorbitol in such a way that the organic solvent penetrated into the porous structure of the sorbitol and the organic solvent was immediately removed therefrom by reducing the pressure. Also, the organic solvent was sprayed in small portions so that the sorbitol can maintain flowability without building a slurry form. In other words, by repeatedly spraying a small amount of the organic solvent whenever the sorbitol is dried after spraying a certain amount of the organic solvent, a proliposomee pharmaceutical composition using the sugar alcohol with an increased surface area and/or porosity encapsulating the Sudan IV as a carrier was obtained.

<Comparative Example 1> Experiment on the Reaction of Water and Sorbitol

By using a sieve (sieve no. 50 and 70), 10 g of a sorbitol with 212-300 μm size was put into a rotary evaporator and 30 ml of water was put thereinto. In case of stirring the resulting mixture at 50 rpm to have the sorbitol and water react with each other, the sorbitol was dissolved in water, thus not maintaining a solid dispersion form. In case of freeze-drying the sorbitol-dissolved solvent in 30 minutes later, the sorbitol having a high viscosity in a semi-solid phase was obtained, but the sorbitol having flowability as a solid phase was not obtained.

<Comparative Example 2> Experiment on the Reaction of a Sorbitol and a Mixed Organic Solvent of Methanol and Water (at a Ratio of 1:1)

A water-mixed organic solvent was prepared by completely mixing methanol and water at a volume ratio of 1:1 (v/v). By using a sieve (sieve no. 50 and 70), 10 g of a sorbitol with 212-300 μm size was put into a rotary evaporator and 30 ml of the prepared water-mixed organic solvent was put thereinto. In case of stirring the resulting mixture at 50 rpm to have the sorbitol and the water-mixed organic solvent reach with each other, the sorbitol was dissolved therein, thus not maintaining a solid dispersion form. In case of drying the water-mixed organic solvent under the reduced pressure in 30 minutes later, the sorbitol having a high viscosity in a semi-solid phase was obtained, but the sorbitol having flowability as a solid phase was not obtained.

<Comparative Example 3> Experiment on the Reaction of a Sorbitol and a Mixed Organic Solvent of Chloroform and Water (at a Ratio of 1:1)

A water-mixed organic solvent was prepared by completely mixing methanol and water at a volume ratio of 1:1 (v/v). Instead of the freeze-drying method of Comparative Example 1, a spray-drying method was used and the remaining conditions were the same as Comparative Example 1. The sorbitol having a high viscosity in a semi-solid phase, the same as Comparative Example 1 was obtained, but the sorbitol having flowability as a solid phase was not obtained.

<Comparative Examples 4 to 6> Experiment on the Reaction of a Sorbitol and Water or a Water-Mixed Organic Solvent Instead of the freeze drying and drying under the reduced pressure method of Comparative Example 1, a spray-drying method was used and the remaining conditions were the same as Comparative Example 1. In result, an acicular-shaped crystalline sorbitol having a high viscosity in a semi-solid phase was obtained, but a sorbitol having flowability as a solid phase was not obtained [water (Comparative Example 4), a mixed solvent of methanol and water (at a ratio of 1:1) (Comparative Example 5) and a mixed solvent of chloroform and water (at a ratio of 1:1) (Comparative Example 6)].

<Experimental Example 1> Observation of a Surface Area with a Scanning Electron Microscope (SEM) and an Optical Microscope Each surface area of a sorbitol, mannitol and xylitol obtained from Example 1 and Examples 3 to 14 and Comparative Example and each surface area of a conventional sorbitol, mannitol and xylitol were observed by using an scanning electron microscope (Carl Zeiss, Germany; Jeol, Japan), and the results thereof were illustrated in FIGS. 1 to 6 as shown in Table 1.

TABLE 1

| | | |
|---|---|---|
| FIG. 1 | A | Conventional sorbitol |
| | B | Example 1 |
| | C | Example 3 |
| | D | Example 4 |
| | E | Example 5 |
| | F | Example 6 |
| FIG. 2 | A | Conventional mannitol |
| | B | Example 7 |
| FIG. 3 | A | Conventional xylitol |
| | B | Example 8 |
| | C | Example 9 |
| FIG. 4 | A | Example 10 |
| | B | Example 11 |
| FIG. 5 | A | Example 12 |
| | B | Example 13 |
| | C | Example 14 |
| FIG. 6 | A | Example 11 |
| | B | Comparative Example 5 |

It is confirmed that the sorbitol prepared in Example 1 (FIG. 1-B) was so changed that a surface structure thereof built a net-shaped form in comparison with the conventional sorbitol (FIG. 1-A). In other words, a porosity and/or surface area of the solid sorbitol particle was significantly increased. According to Examples 3 to 9, each of the scanning electron microscope (SEM) images showed a difference in the porosity and/or surface area, but it is found that the surface area and/or porosity was increased through a contact reaction in which a sugar alcohol such as sorbitol (FIGS. 1-C, D, E and F), mannitol (FIG. 2-B), xylitol (FIGS. 3-B and C) and so on maintained a solid dispersion with each of the solvents.

According to scanning electron microscope (SEM) images (FIGS. 4-A and B) of Examples 10 and 11, it is shown that a surface area and/or porosity of sorbitol were increased by means of a reaction with a mixed solvent of methanol and water. In contrast, according to a preparing method of Comparative Example 5, in which a water-mixed solvent of methanol and water (at a ratio of 1:1) was used, if a sorbitol was dissolved therein to react not in a solid dispersion but in a solvent state, even after the solvent was removed therefrom through a method such as a spray-drying, an acicular-shaped sorbitol having no flowability, but high viscosity in a semi-solid phase was obtained as shown in FIG. 6, the sugar alcohol having flowability as a solid phase was not prepared.

Therefore, the reaction conditions such as a selected type and ratio of a solvent, a reaction time, etc., according to a type and amount of a sugar alcohol, need to be modified so that the sugar alcohol cannot be completely dissolved, but maintain a solid dispersion.

Each of the FIGS. 5-A, B and C is a scanning electron microscope (SEM) image of a sorbitol prepared in Examples 12 to 14, that is, the sorbitol with a decreased surface area and/or porosity, in which a conventional sorbitol was not dissolved but reacted as a solid dispersion in a solvent including chloroform or a solvent including the same. FIG. 5-A shows that a porous structure disappeared from a surface of the sorbitol just through a reaction with chloroform for one minute and a surface of the sorbitol became smooth by means of a mixed solvent of chloroform and methanol (FIG. 5-B) or a mixed solvent of chloroform and water (FIG. 5-C), so the surface area and/or porosity of the sorbitol was decreased in comparison with the conventional sorbitol (FIG. 1-A). In other words, it is possible to prepare the sugar alcohol with a decreased surface area and/or porosity by using a non-polar solvent such as chloroform and it is also necessary to adjust the reaction conditions such as a selected type and ratio of a solvent, a reaction time, etc., according to a type and amount of a sugar alcohol so that the sugar alcohol cannot be completely dissolved therein and maintain a solid dispersion during a reaction.

Figure 7:
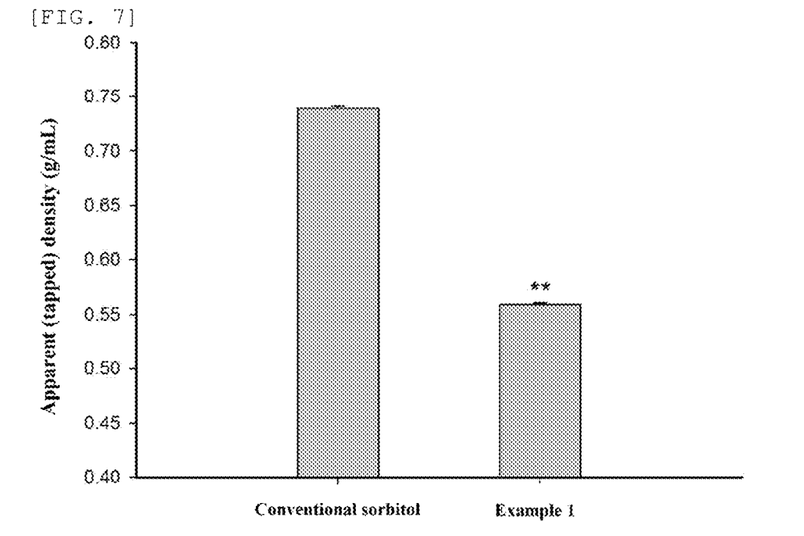
FIG. 7 is a graph of comparing an apparent (tapped) density between a conventional sorbitol and a sorbitol prepared according to a preparing method of Example 1 of the present disclosure.

<Experimental Example 2> Measurement of Apparent (Tapped) Density, True Density and Specific Surface Area A conventional sorbitol with 212-300 μm size obtained by using a sieve (sieve no. 50 and 70) as provided in the $10^{th}$ Revision of Korean Pharmacopeia and a sorbitol with an increased porosity prepared in Example 2 were prepared by 2.5 to 4 g respectively, put into a precision measuring cylinder (10 mL), and manually tapped (at a height of 3 cm 100 times for one minute), thus measuring a precise mass of each sorbitol having 5 mL in volume and measuring an apparent density accordingly. In other words, if there is a mass difference in each sorbitol particle having the same size range and the same volume, it is meant that the particle has a different porosity and a particle with a relatively small apparent density has a higher porosity. As shown in FIG. 7, an apparent density of a conventional sorbitol was 0.739±0.002 g/ml (mean±SD, n=3), but an apparent density of the sorbitol prepared in Example 1 was 0.559±0.002 g/ml, which accounted for 75.6% of the conventional sorbitol. Thus, it is found that the sorbitol of the present disclosure has a significantly increased porosity.

Such an increase in porosity was reconfirmed in the measurement of a specific surface area. The specific surface area was measured by using a multi-point (7-point) BET instrument (Quantasorb-SI; Quantachrome Instruments) in such a way that nitrogen gas was respectively absorbed into a conventional sorbitol of 212-300 μm size obtained by using a sieve (sieve no. 50 and 70) as provided in the $10^{th}$ Revision of Korean Pharmacopeia as well as the sorbitol with an increased porosity prepared in Examples 1 and 2. A specific surface area of the conventional sorbitol was 1.56 $m^2$/g, a specific surface area of the sorbitol of Example 1 was 3.73 $m^2$/g, and a specific surface area of the sorbitol of Example 2 was 4.17 $m^2$/g. Thus, the specific surface areas of the sorbitols of the present disclosure were increased 239% and 267%, respectively.

Figure 8:
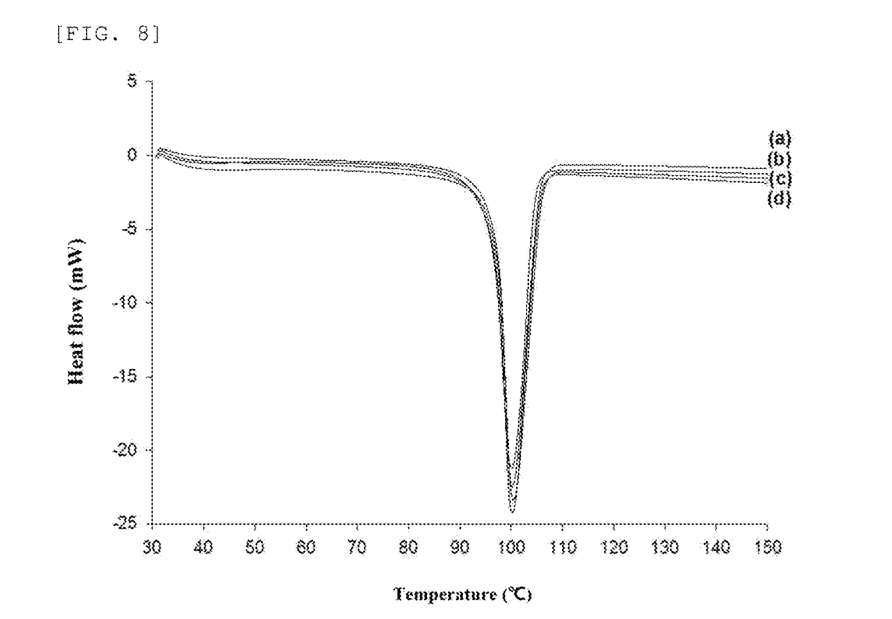
FIG. 8 is a result of measuring a conventional sorbitol (a) and a sorbitol prepared according to a preparing method of the present disclosure (Example 1(b), Example 2(c) and Example 13(d)) by using a differential scanning calorimetry (DSC).

Although the apparent density and the specific surface area were increased, as a result of measuring a true density of the conventional sorbitol and the sorbitols of Examples 1 and 2 by using helium gas and a pycnometer (ULTRAPYC 1200e; Quantachrome Instruments, Boynton Beach, Fla.), it is found that the true density thereof were 1.49, 1.51, 1.51 g/ml respectively without a difference. There was no difference in a calorimetry curve as a result (FIG. 8) of measuring the conventional sorbitol (FIG. 8-a) and the sorbitols of Example 1 (FIG. 8-b), Example 2 (FIG. 8-c) and Example 13 (FIG. 8-d) in such a way that a differential scanning calorimetric (DSC) (DSC-60; Shimadzu, Kyoto, Japan) was increased by 101 per minute from 30° C. to 150° C. Thus, it is found that the sugar alcohol with a modified surface area and/or porosity has only a changed surface area and/or porosity from the conventional sugar alcohol, but does not have a changed physicochemical property therefrom.

<Experimental Example 3> Analysis of a Drug (Sudan IV) Content in a Carrier

Each content of a drug (Sudan IV) contained in a proliposomee pharmaceutical composition prepared in Example 15 by using the sorbitol of Example 1 and a proliposomee pharmaceutical composition prepared in the same method as Example 15 by using a conventional sorbitol was analyzed by using an UV analysis method (Lambda 25; PerkinElmer Inc., Waltham, Mass.) (540 nm).

Figure 9:
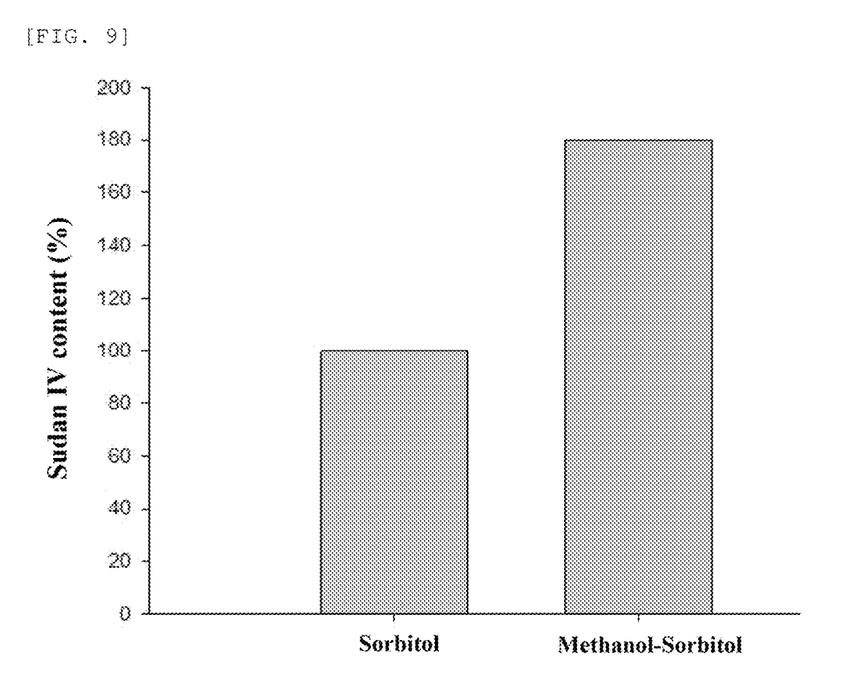
FIG. 9 is a graph of indicating a ratio of a drug contained in a proliposomee, in case a drug (Sudan IV) is encapsulated respectively by a conventional sorbitol and a sorbitol prepared after reacting with methanol according to the present disclosure (Example 1).

As shown in FIG. 9, the composition using the sorbitol of the present disclosure shows a significant increase of 182% in a drug content in comparison with the composition by the conventional sorbitol (100%), suggesting that the sorbitol of the present disclosure has a significantly increased surface area and/or porosity.

INDUSTRIAL APPLICABILITY

A sugar alcohol prepared by a preparing method of the present disclosure has a modified surface area and/or porosity in comparison with a conventional sugar alcohol. Therefore, if the sugar alcohol containing each component is as a carrier, a coating object, etc., or as a component of compositions for drugs, food, cosmetics, feed, etc., a ratio of an active ingredient to the carrier can be modified, so that the sugar alcohol can be used in preparing of formulations or compositions.

What is claimed is:

1. A method for preparing a sugar alcohol with a modified surface area and/or porosity while having flowability as a solid phase, the method, comprising:
   (A) reacting the sugar alcohol in a solid state with a solvent (S), in which the sugar alcohol is not dissolved by the solvent (S) and is reacted with the solvent (S) as a solid dispersion; and
   (B) removing the solvent (S) therefrom,
   wherein the solvent (S) is an organic solvent (S-1) or a water-mixed organic solvent (S-2),
   wherein the organic solvent (S-1), which has to be used at a ratio of less than 30 mL of the organic solvent (S-1) to 1 g of the sugar alcohol so as not to dissolve the sugar alcohol, is a single or mixed solvent, and the water-mixed organic solvent (S-2) is a mixed solvent of water and the organic solvent (S-1), in which a ratio of water is less than 50% (v/v) of the total solvent.

2. The method of claim 1, wherein the modified surface area is an increased surface area, and wherein the organic solvent (S-1) is a polar organic solvent.

3. The method of claim 2, wherein a polarity of the organic solvent (S-1) is 30 to 90% (v/v) of water.

4. The method of claim 2, wherein the organic solvent (S-1) is C1-C5 alcohols, C6-C10 aromatic alcohols, C1-C5 amino alcohols, C1-C4 carboxylic acids, C1-C4 amides, or a mixture thereof.

5. The method of claim 1, wherein the modified surface area is a decreased surface area, and wherein the organic solvent (S-1) is a non-polar organic solvent.

6. The method of claim 5, wherein the organic solvent (S-1) is chloroform or a mixed solvent including the same.

7. The method of claim 1, wherein the sugar alcohol is mannitol, sorbitol, xylitol, erythritol, arabitol, maltitol, inositol, lactitol, isomalt, fucitol, or a mixture thereof.

8. The method of claim 1, wherein a reaction time of the step (A) is one or more minutes.

9. The method of claim 1, wherein a reaction time of the step (A) is one hour or less.

10. The method of claim 1, wherein a reaction of the step (A) is to mix or stir the sugar alcohol and the solvent (S).

11. The method of claim 1, wherein the step (B) is performed with drying at room temperature, hot air drying, freeze-drying, drying under a reduced pressure, or a combination thereof.

12. A pharmaceutical composition prepared by the method of claim 1, wherein the pharmaceutical composition comprises a sugar alcohol with an increased surface area and/or porosity while having flowability as a solid phase.

13. A cosmetic composition prepared by the method of claim 1, wherein the cosmetic composition comprises a sugar alcohol with a modified surface area and/or porosity while having flowability as a solid phase.

* * * * *